(12) United States Patent
Wiessler et al.

(10) Patent No.: US 6,521,604 B1
(45) Date of Patent: Feb. 18, 2003

(54) COMPOUNDS CONTAINING BORON FOR ENERGY-FILTERING TRANSMISSION ELECTRON MICROSCOPY AND FOR BORON NEUTRON-CAPTURE THERAPY

(75) Inventors: Manfred Wiessler, Frankenthal (DE); Helmut Tröster, Mannheim (DE); Stefan Raddatz, Heidelberg (DE); Eberhard Spiess, Ladenburg (DE); Michael Trendelenburg, Dossenheim (DE)

(73) Assignee: Deutches Krebsforschungszentrum, Heidelberg (DE)

( * ) Notice: Subject to any disclaimer, the term of this patent is extended or adjusted under 35 U.S.C. 154(b) by 0 days.

(21) Appl. No.: 09/601,373

(22) PCT Filed: Jan. 27, 1999

(86) PCT No.: PCT/DE99/00257
§ 371 (c)(1),
(2), (4) Date: Dec. 15, 2000

(87) PCT Pub. No.: WO99/38870
PCT Pub. Date: Aug. 5, 1999

(30) Foreign Application Priority Data

Jan. 28, 1998 (DE) ................................. 198 03 206

(51) Int. Cl.[7] .............................. A61K 31/69; C07F 5/02
(52) U.S. Cl. .................................. 514/64; 568/4; 568/5
(58) Field of Search .................... 568/3, 4, 5; 514/64

(56) References Cited

U.S. PATENT DOCUMENTS 3,376,346 A  *  4/1968  Schwartz et al.
3,395,182 A  *  7/1968  Hansjuergen
6,037,490 A  *  3/2000  Kabalka et al. ................. 562/7

OTHER PUBLICATIONS

CA:125:195765 abs of Inorg Chem by Jiang et al 35(19) pp 5417–5426 1996.*
CA:125:59070 abs of Angew Chem Int Ed Engl by Qualmann et al 35(8) pp 909–911 1996.*

* cited by examiner

Primary Examiner—Jean F. Vollano
(74) Attorney, Agent, or Firm—Albert P. Halluin; Viola T. Kung; Howrey, Simon, Arnold & White, LLP

(57) ABSTRACT

The invention relates to a compound which contains boron and which comprises the following general formula (1)

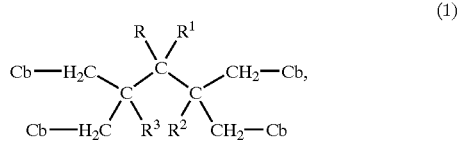

in which
Cb represents carborane,
$R^2$ and $R^3$, independent of one another, represent a hydrogen atom or an organic radical, and
R and $R^1$, independent of one another, represent a hydrogen atom or an organic group, or R and $R^1$ form a carbonyl group with the carbon atom to which they are bound.

The invention also relates to a method of producing a compound containing boron and to the application of the same.

13 Claims, 1 Drawing Sheet

COMPOUNDS CONTAINING BORON FOR ENERGY-FILTERING TRANSMISSION ELECTRON MICROSCOPY AND FOR BORON NEUTRON-CAPTURE THERAPY

This application is a National State of International Application PCT/DE99/00257, filed Jan. 27, 1999; which claims the priority of DE 198 03 206.4, filed Jan. 28, 1998.

The invention relates to compounds containing boron, their production and the use thereof for the energy-filtering transmission electron microscopy and for the boron neutron-capture therapy.

It is known to detect boron-containing compounds by the energy-filtering transmission electron microscopy (EFTEM).

For example, Qualmann B. et al., *Angew. Chem.*, 1996 180, pages 970 to 973, describes the synthesis of boron-containing lysine dendrimers for protein labeling in electron microscopy. The boron-containing compound described in this publication and serving for labeling proteins is unsuitable for labeling small biological molecules, e.g. oligonucleotides, because of its large expansion, since the material properties of such small biological molecules are modified excessively. Furthermore, because of the large expansion of the compound and the arrangement of the 1,2-dicarbadodecaborane fragments (carboranes) in the outermost sphere of the molecule the boron density is very low. Therefore, a specification of this compound by means of EFTEM is not possible to a satisfactory extent. In addition, the described compound has a peptide base structure with L-lysine as building blocks, so that it is susceptible to enzymatic degradation.

The publication by Newkome G. R. et al., in *Angew. Chem.*, 1994, 106, pages 701 to 703, describes unimolecular micelles, which contain 4 or 12 carboranes in the micelle interior and hydrophilic groups on the surface of the micelles. These unimolecular micelles are also too big. Furthermore, no binding site exists for the linkage of a spacer for attachment to biomolecules, such as oligonucleotides and proteins.

Therefore, it was formerly not possible to label for detection by EFTEM small biologically active substances, such as oligonucleotides, by a boron-containing compound to be bonded covalently.

It is also known to use boron-containing compounds in the boron neutron-capture therapy. However, it was not yet possible to selectively introduce sufficiently high boron concentrations into the tumor tissue.

Thus, the object of this invention is to provide a compound which does not show the drawbacks of the prior art.

According to the invention this is achieved by the subject matters defined in the claims.

The subject matter of the present invention relates to a boron-containing compound which has the following general formula (1)

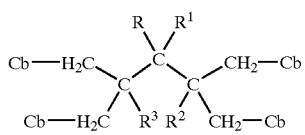

(1)

in which
Cb stands for a carborane,
$R^2$ and $R^3$ are independently a hydrogen atom or an organic residue, and R and $R^1$ are independently a hydrogen atom or an organic residue with the carbon atom to which they are bound.

The expression "carborane" comprises compounds of any kind, which include the summation formula $B_{10}C_2H_{12}$. The carboranes may form three isomers: 1,2-dicarba-closo-dodecaborane, 1,7-dicarba-closo-dodecaborane, and 1,12-dicarba-closo-dodecaborane, which are also referred to as ortho-, meta-, and para-carborane. Of these isomers the 1,2-dicarba-closo-dodecaborane is preferred, which is symbolized as follows:

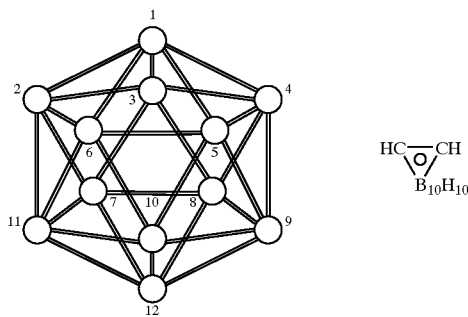

Because of the two carbon atoms the carboranes have two possible binding sites with other compounds. Due to the linkage of the four carboranes with the hydrocarbon skeleton indicated in formula (1) one binding site of the carborane is occupied. The second binding site can now be used for binding spacers and/or solubility-modulating compounds.

The expression "spacer" comprises compounds of any kind, which can be used for linkage, in particular for covalent linkage, of the boron-containing compound according to the invention with other molecules, e.g. with biological molecules. Such compounds are known to a person skilled in the art. They are preferably compounds derived from C2 to C10 alkanes, in particular C6 alkanes, which are preferably linear and optionally have ether bridges or may be bound via such a bridge to the carborane. The expression "biological molecules" refers to the fact that any kind of molecule relevant for biological processes is concerned. Examples are proteins, nucleotides, such as mono-, oligo-, and polynucleotides, nucleosides, nucleoside diphosphates and nucleoside triphosphates. Of the proteins those are preferred which accumulate in tumors, such as albumin.

The "solubility-modulating compounds" are compounds of any kind, which raise or lower the solubility of the compound according to the invention in a solvent, in particular water or an aqueous solvent. To raise the water solubility, the solubility-modulating compounds may have at least one polar group, such as a hydroxyl group. Examples thereof are —$CH_2OH$ and polyhydroxy compounds, such as inositol or saccharides, in particular monosaccharides, preferably glucose. Because of the high degree of lipophilia of the carboranes and the hydrocarbon skeleton the bonding of solubility-modulating compounds is favorable for raising the water solubility of the boron-containing compound.

By the use of carbohydrates, in particular glucose, galactose, xylose, fucose or also gentiobiose the tumor selectivity of the boron-containing compound according to the invention can also be increased.

Examples of compounds in which glucose is bound to the carboranes are the compounds shown in formulae (2) and (3).

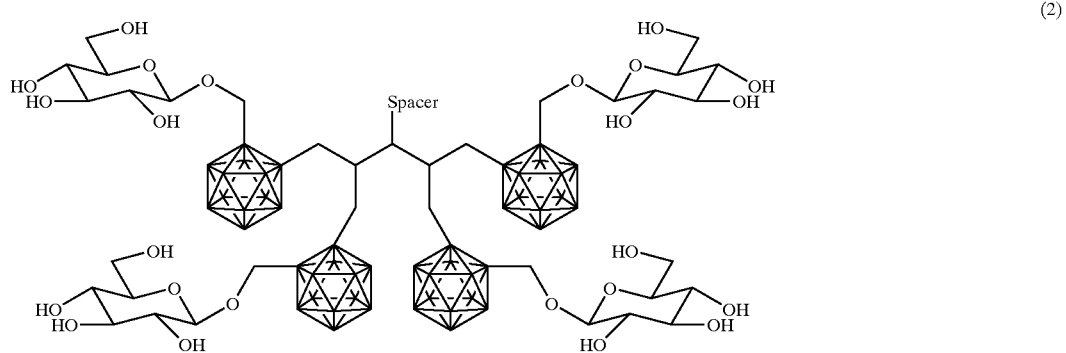

(2)

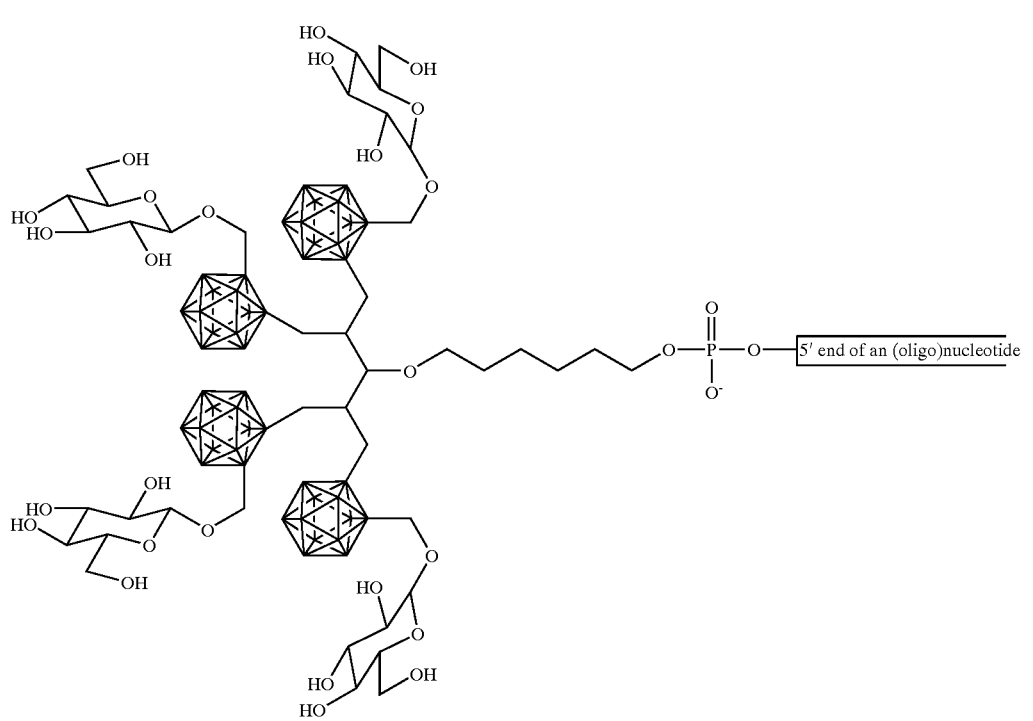

(3)

This serves for obtaining small lipophilic molecule cores in which the entire boron amount is concentrated and a hydrophilic molecule shell which increases the water solubility of the boron-containing compound and optionally the tumor selectivity. All in all, a unimolecular micelle is thus obtained.

In the boron-containing compound according to the invention, the substituents $R^2$ and $R^3$ are independently a hydrogen atom or an organic residue. The expression "organic residue" covers organic compounds of any kind, which comprise carbon, hydrogen and optionally oxygen, sulfur, phosphorus and boron. Examples thereof are the groups —$NO_2$, —(C=O)—, —C≡N—, phenyl and —$COOR^4$, wherein $R^4$ represents e.g. an alkyl residue such as ethyl. $R^2$ and $R^3$ can also be linked with each other, i.e. the residues denoting $R^2$ and $R^3$ are chosen such that they form a ring, preferably a 6-membered ring, with the carbon atoms to which they are directly bound and with the carbon atom including the residues R and $R^1$. Further carboranes can be bound to the ring, so that the total number of carboranes in the compound according to the invention is increased, e.g. to 6. Examples of $R^2$ and $R^3$ for forming a 6-membered ring are:

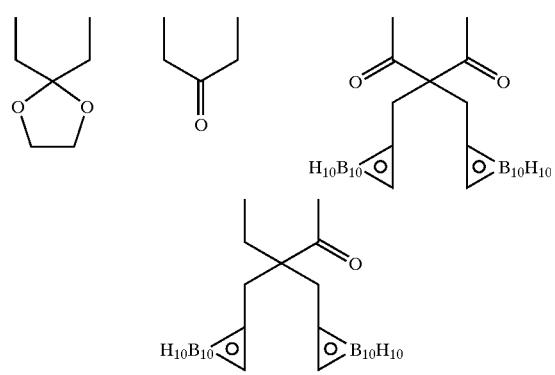

In the boron-containing compound according to the invention, the substituents R and $R^1$ are independently a hydrogen atom, an organic group or R and $R^1$ form a carbonyl group together with the carbon atom to which they are bound. The organic group can be every compound containing carbon, hydrogen and optionally oxygen, sulfur, phosphorus and boron. For example, the group is a C2 to C10, in particular C6, alkyl group bound via an ether bridge. A phosphate group ($PO_4^{3-}$) can be bound to the alkyl group, in particular to the end thereof. The phosphate group can be bound to a biological molecule, such as a poly-, oligo- or mononucleotide, preferably at the 51 ends thereof. An example of such an organic group standing for R and $R^1$, respectively, is shown in above formula (3).

Another subject matter of the present invention relates to a method of producing the boron-containing compounds according to the invention, in which a decaborane is reacted with an alkyne of formula (4).

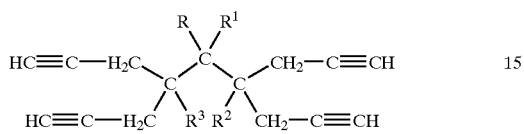

A decaborane is a compound with the summation formula $B_{10}H_{14}$, which differs from the above described carboranes in that inter alia the two carbon atoms are not present. They are introduced by the two carbon atoms of the alkyne bond.

It was found surprisingly that this reaction will also be possible if at least four carboranes are bound to a very small hydrocarbon base structure in spite of the steric impediment. It was also found that surprisingly high yields will be obtained if a carbonyl group is disposed in the β-position relative to the alkyne group. If necessary, the carbonyl group can be protected as usual and then be deprotected also in known manner.

Examples of this reaction are shown in the reaction equations (I) to (VI).

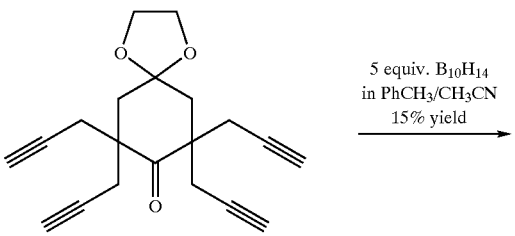
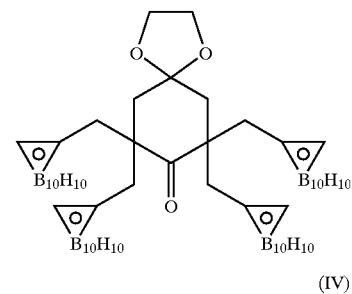
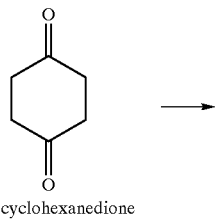
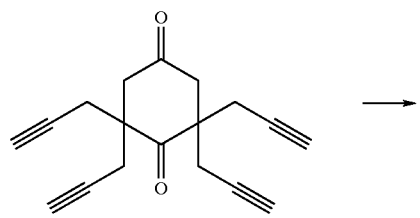
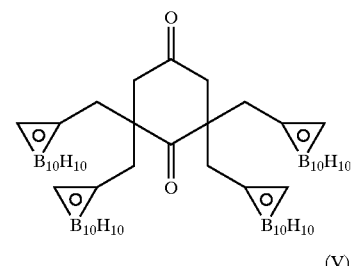
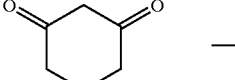
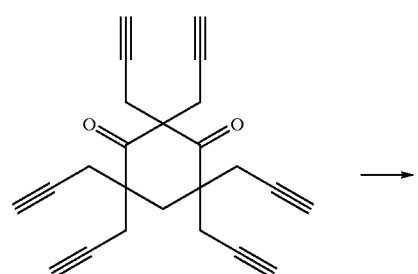
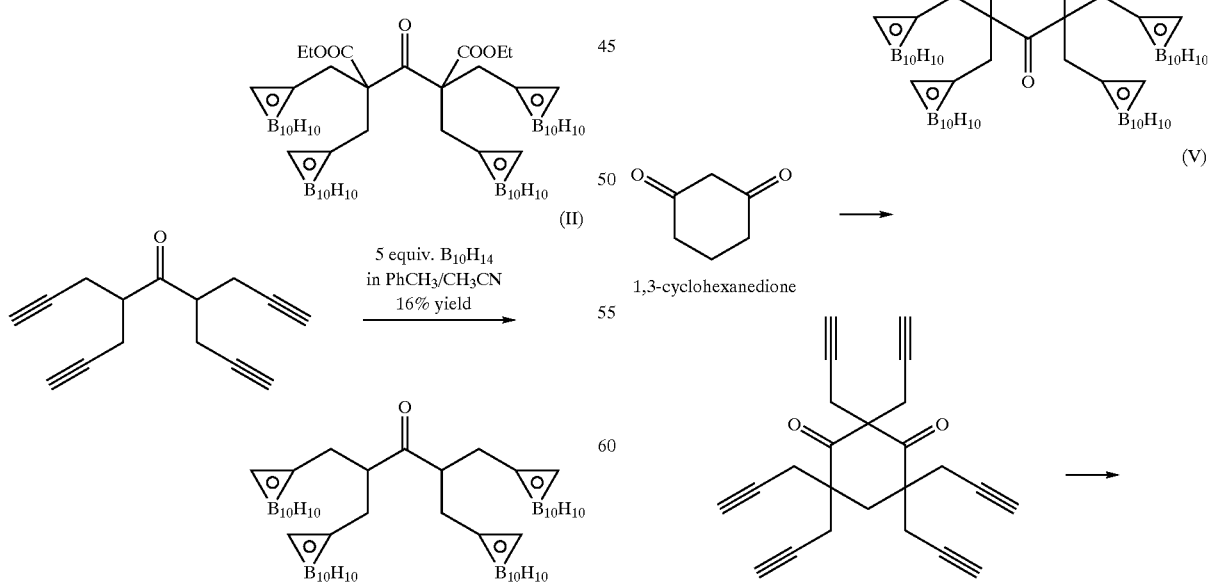

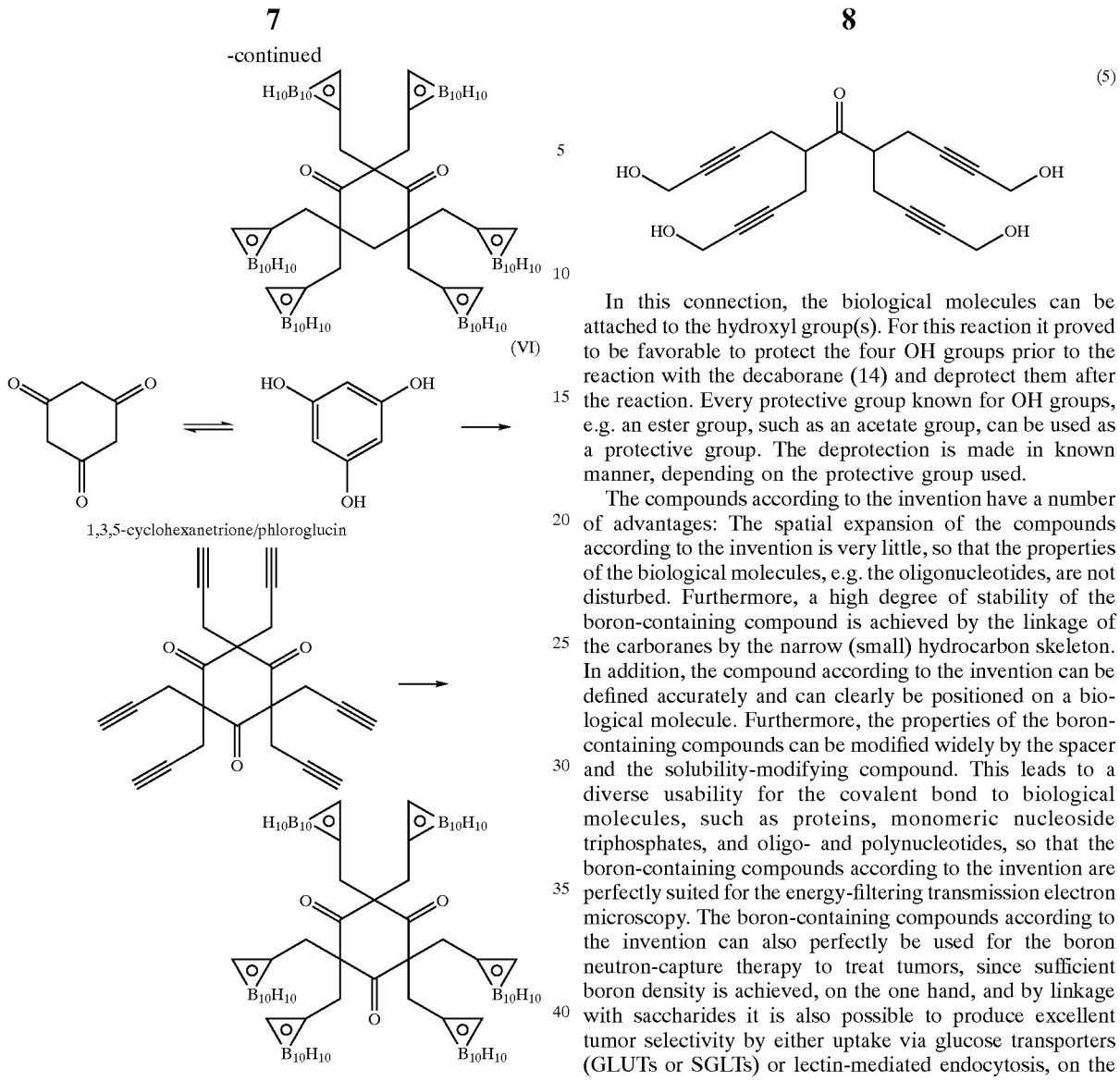

The alkyne compounds can be produced from CH-acidic carbonyl compounds in a manner with which the person skilled in the art is familiar. This is carried out e.g. by means of C alkylation of enolates of esters or ketones which can be produced by deprotonation using suitable bases, such as aqueous caustic soda solution, under phase transfer catalysis or sodium methylate in methanol and are reacted with a proparyl halide, such as proparyl bromide.

The resulting boron-containing compounds according to the invention offer per carborane a further position for introducing the above-mentioned spacers or solubility-modulating compounds, such as saccharides, in particular glucose. The carbonyl group(s) can then be used for binding an above described spacer and thus for linkage to biological molecules and solubility-modulating compounds. For this purpose, the carbonyl group can be reduced with respect to the alcohol, e.g. by means of LiAlH$_4$ followed by the formation of an ether group.

Alkynes which already have side chains for the linkage of biological molecules, e.g. saccharides, can also be used for the process according to the invention for producing boron-containing compounds. Such a starting compound is indicated in formula (5).

In this connection, the biological molecules can be attached to the hydroxyl group(s). For this reaction it proved to be favorable to protect the four OH groups prior to the reaction with the decaborane (14) and deprotect them after the reaction. Every protective group known for OH groups, e.g. an ester group, such as an acetate group, can be used as a protective group. The deprotection is made in known manner, depending on the protective group used.

The compounds according to the invention have a number of advantages: The spatial expansion of the compounds according to the invention is very little, so that the properties of the biological molecules, e.g. the oligonucleotides, are not disturbed. Furthermore, a high degree of stability of the boron-containing compound is achieved by the linkage of the carboranes by the narrow (small) hydrocarbon skeleton. In addition, the compound according to the invention can be defined accurately and can clearly be positioned on a biological molecule. Furthermore, the properties of the boron-containing compounds can be modified widely by the spacer and the solubility-modifying compound. This leads to a diverse usability for the covalent bond to biological molecules, such as proteins, monomeric nucleoside triphosphates, and oligo- and polynucleotides, so that the boron-containing compounds according to the invention are perfectly suited for the energy-filtering transmission electron microscopy. The boron-containing compounds according to the invention can also perfectly be used for the boron neutron-capture therapy to treat tumors, since sufficient boron density is achieved, on the one hand, and by linkage with saccharides it is also possible to produce excellent tumor selectivity by either uptake via glucose transporters (GLUTs or SGLTs) or lectin-mediated endocytosis, on the other.

Figure 1:
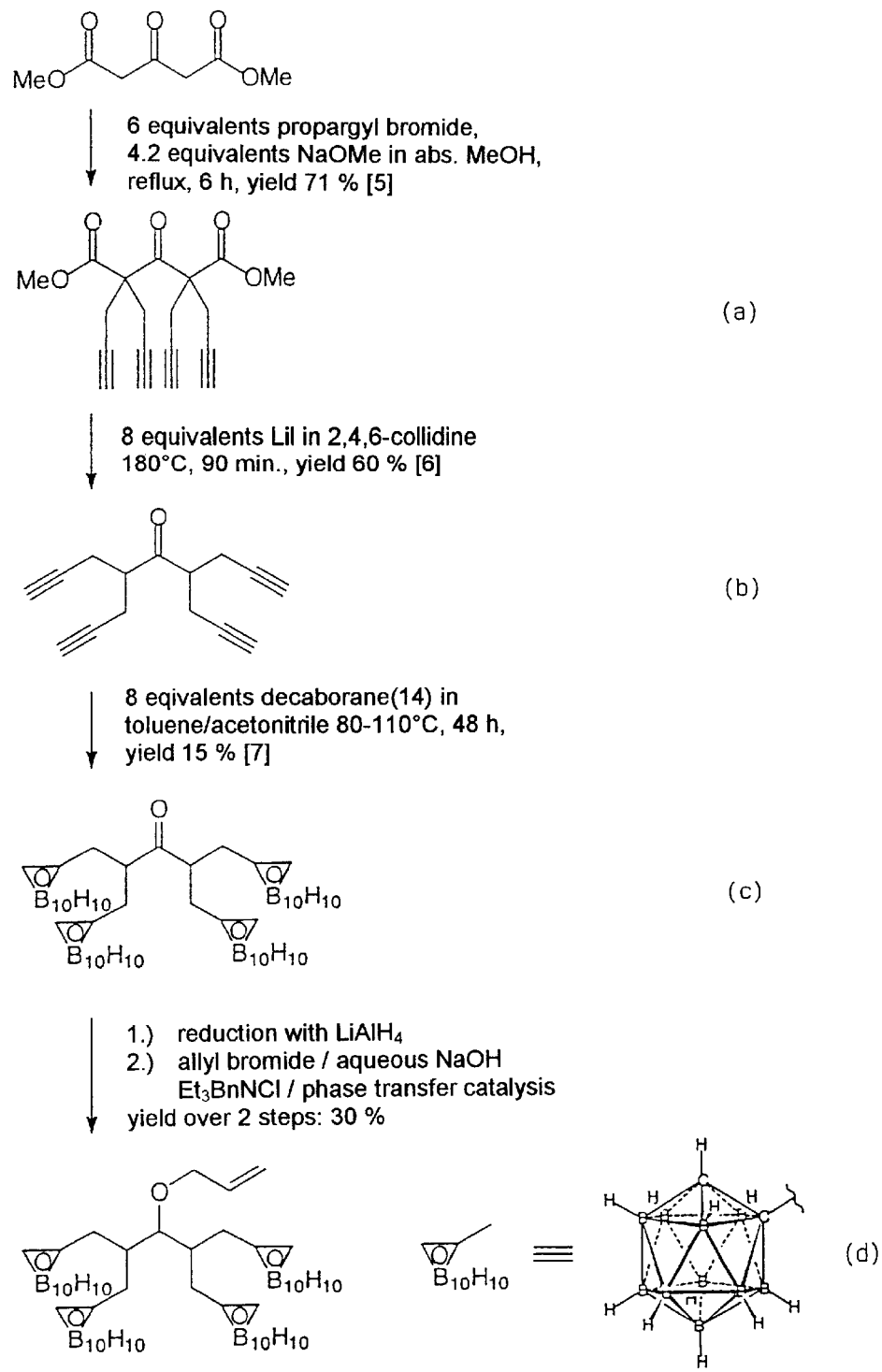
FIG. 1 shows the production of a boron-containing compound according to the invention.

The below example explains the invention:

EXAMPLE

Production of 2-allyloxy-1,1,3,3-tetrakis(closo-1,2-dicarbadodecaboranylmethyl)propane The scheme for the production of the above-mentioned compound is shown in FIG. 1.

(a) 2,2,4,4-tetrapropargylacetonedicarboxylic acid dimethyl ester 238 mg (1.37 mmol) acetonedicarboxylic acid dimethyl ester, 0.90 ml (8.0 mmol) of an 80% solution of propargyl bromide in toluene and 0.5 ml of a 5.4 molar (2.7 mmol) sodium methylate solution in methanol were dissolved in an argon atmosphere in dry methanol (molecular sieve 3 angstrom). Refluxing was carried out for 1 h, then another 0.5 ml sodium methylate solution in methanol was added to the reaction mixture and refluxing was carried out for another 5 h. The reaction mixture was allowed to cool down and mixed with dilute hydrochloric acid in excess. Extraction with diethyl ether was carried out three times, the organic phases were combined, washed with water and dried over anhydrous sodium sulfate. The solvent was removed on the rotary evaporator and the residue was distilled with water jet vacuum in the bulb tube furnace. A colorless oil separated at 220° C. in the receiving flask, which crystallized in the cold and was identified as the desired product by means of $^1$H and $^{13}$C NMR spectroscopy. Yield: 321 mg (0.985 mmol, 71% of the theoretical).

(b) 1,1,3,3-tetraproparqyl acetone 97.0 mg (0.297 mmol) 2,2,4,4-tetrapropargylacetone dicarboxylic acid dimethyl ester and 343 mg (2.56 mmol) lithium iodide in 2,4,6-collidine were heated in argon at 180° C. for 90 min. The mixture was allowed to cool down and 5 ml 15% hydrochloric acid were added. A layer of diethyl ether was placed thereabove. Water was added with vigorous stirring until the aqueous phase turned clear. The organic phase was separated, the aqueous phase was extracted another three times with ether. The organic phases were combined and washed in succession with 5% sodium hydroxide solution, water and saturated sodium chloride solution. Drying was carried out over anhydrous sodium sulfate. The solvent was distilled off on the rotary evaporator, the remaining residue solidified into a colorless solid. This solid was distilled in the water jet vacuum. Colorless needles separated in the receiving flask at 220° C., which could be identified as the desired product by means of $^1$H and 13C NMR spectroscopy. Yield: 38.0 mg (0.180 mmol, 60.6% of the theoretical).

(c) 1,1,3,3-tetrakis (closo-1,2-dicarbadodecaboranylmethyl)-acetone 177 mg (0.842 mmol) 1,1,3,3-tetrapropargylacetone, 542 mg (4.44 mmol) decaborane, and 440 mg (10.2 mmol) dry acetonitrile in 5 ml dry toluene were heated in argon at 80° C. for 16 h, then at 100° C. for 4 h and finally at 120° C. for 4 h. The heating bath was allowed to cool down to 100° C. Excess decaborane (14) was destroyed by adding a 1/1 (v/v) mixture of concentrated hydrochloric acid and ethanol and refluxing for 6 hours. The organic phase was separated, the aqueous phase was extracted two more times with toluene. The organic phases were combined, washed with water, dried over anhydrous sodium sulfate and concentrated on the rotary evaporator. The residue was chromatographed over silica gel with petroleum ether/acetic ethyl ester in a ratio of 4/1, and 87 mg of a colorless oil were obtained which crystallized in the cold. $^1$H and $^{13}$C NMR spectrum and ESI mass spectrum confirmed the desired structure. Yield: 87.1 mg (0.128 mmol, 15.2% of the theoretical).

(d) 2-allyloxy-1,1,3,3-tetrakis(closo-1,2-dicarbadodecaboranylmethyl)propane 5,1 mg lithium aluminum hydride in dry ether were suspended in argon and a solution of 21.5 mg (31.5 μmol) 1,1,3,3-tetrakis(closo-1,2-dicarbadodecaboranyl-methyl) acetone in dry ether were added drop-wise. Stirring was carried out at room temperature for 30 min, and then refluxing was effected for 1 h. The mixture was allowed to cool down and excess lithium aluminum hydride was destroyed by drop-wise addition of water. Then, 10% sulfuric acid was added drop-wise with stirring until all deposits are dissolved. The organic phase was separated and the aqueous phase was extracted twice with ether. The organic phases were combined, washed with water and dried over anhydrous sodium sulfate. The solvent was evaporated off and the residue was dissolved in 0.50 ml (6.0 mmol) allyl bromide. For this purpose, a solution of 80 mg (2.0 mmol) sodium hydroxide and 17 mg (75 μmol) benzyltriethylammonium chloride in 1 ml water were added and stirred vigorously at room temperature for 16 h. Thereafter, the mixture was diluted with 2 ml water, and 2 ml ether were added. The organic phase was separated and the aqueous phase was extracted two times with ether. The organic phases were combined, washed with water and dried over anhydrous sodium sulfate. The solvent was withdrawn on the rotary evaporator and the residue was chromatographed over silica gel with petroleum ether/acetic ethyl ester in a ratio of 4/1. 6.9 mg of a colorless highly viscous oil were isolated which was identified by $^1$H and $^{13}$C NMR spectroscopy as the desired product. Yield: 6.9 mg (9.5 μmol, 30% of the theoretical).

What is claimed is:

1. A boron-containing compound which comprises the following general formula (1)

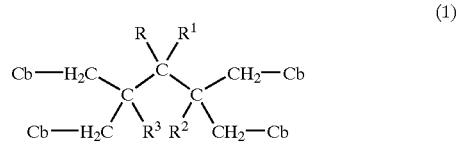

in which

Cb represents a carborane, $R^2$ and $R^3$, independent of one another, represent a hydrogen atom or an organic residue, and R and $R^1$, independent of one another, represent a hydrogen atom or an organic residue, or R and $R^1$ form a carbonyl group with the carbon atom to which they are bound, wherein the carborane is 1,2-dicarba-closo-dodecaborane.

2. The compound according to claim 1, wherein a spacer and/or a solubilizing-modulating compound is bound to the carborane.

3. The compound according to claim 2, wherein the solubility-modulating compound is glucose.

4. The compound according to claim 2, wherein a solubility-modulating compound is bound to at least one carborane.

5. The compound according to claim 1, wherein $R^2$ and $R^3$ are independently a $COOR^4$ group, and $R^4$ represents an alkyl residue, or $R^2$ and $R^3$ together with the carbon atoms to which they are bound form a 6-membered ring.

6. The compound according to claim 5, wherein for forming the 6-membered ring $R^2$ and $R^3$ are selected from the group consisting of:

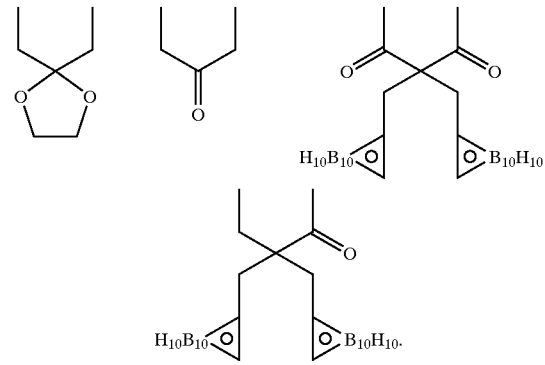

7. The compound according to claim 1, wherein R and $R^1$ are independently a $C_2$ to $C_{10}$ alkoxy group.

8. The compound according to claim 7, wherein a phosphate group is bound covalently to the alkyl group of said $C_2$ to $C_{10}$ alkoxy group.

9. The compound according to claim 8, wherein a mono-, oligo-, or polynucleotide is bound to the phosphate group.

10. A method of producing a compound according to claim 1, comprising the step of reacting a decaborane with a compound of formula (4).

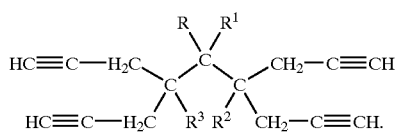

(4)

11. A method for detecting a biologically active compound comprising the steps of:
    labeling a biologically active compound with the boron-containing compound according to claim 1, and
    detecting said labelled biologically active compound by an energy-filtering transmission electron microscopy.

12. A method for treating a tumor disease comprising the steps of:
    introducing the boron-containing compound according to claim 1 into a tumor tissue, and treating the tumor tissue by boron neutron-capture therapy.

13. A boron-containing compound which comprises the following general formula (1)

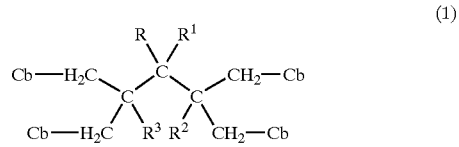

(1)

in which
    Cb represents a carborane,
    $R^2$ and $R^3$, independent of one another, represent a hydrogen atom or an organic residue, and
    R and $R^1$, independent of one another, represent a hydrogen atom or an organic residue, or R and
    $R^1$ form a carbonyl group with the carbon atom to which they are bound,
    wherein the carborane is 1,7-dicarba-closo-dodecarborane or 1,12-dicarba-closo-dodecarborane.

* * * * *

UNITED STATES PATENT AND TRADEMARK OFFICE
CERTIFICATE OF CORRECTION

PATENT NO.   : 6,521,604 B1
DATED        : February 18, 2003
INVENTOR(S)  : Manfred Wiessler et al.

It is certified that error appears in the above-identified patent and that said Letters Patent is hereby corrected as shown below:

<u>Title page,</u>
Item [73], Assignee, change "Deutches" to -- Deutsches --.

Signed and Sealed this

Sixteenth Day of September, 2003

JAMES E. ROGAN
*Director of the United States Patent and Trademark Office*